United States Patent
Knauf et al.

(10) Patent No.: US 10,851,048 B2
(45) Date of Patent: Dec. 1, 2020

(54) PROCESS FOR PREPARING AN ISOCYANATE BY PARTLY ADIABATICALLY OPERATED PHOSGENATION OF THE CORRESPONDING AMINE

(71) Applicant: Covestro Deutschland AG, Leverkusen (DE)

(72) Inventors: Thomas Knauf, Dormagen (DE); Christian Steffens, Cologne (DE); Anke Hielscher, Cologne (DE); Dietmar Wastian, Dormagen (DE); Juergen Spriewald, Kölln-Reisiek (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/677,744

(22) Filed: Nov. 8, 2019

(65) Prior Publication Data
US 2020/0148629 A1 May 14, 2020

(30) Foreign Application Priority Data
Nov. 13, 2018 (EP) .................................... 18205954

(51) Int. Cl.
*C07C 263/10* (2006.01)
*C07C 263/20* (2006.01)
*B01J 19/00* (2006.01)
*B01J 19/18* (2006.01)

(52) U.S. Cl.
CPC ......... *C07C 263/10* (2013.01); *B01J 19/0013* (2013.01); *B01J 19/0066* (2013.01); *B01J 19/1812* (2013.01); *B01J 2219/00051* (2013.01); *C07C 263/20* (2013.01)

(58) Field of Classification Search
CPC .. C07C 263/10; C07C 263/20; B01J 19/0013; B01J 19/0066; B01J 19/1812; B01J 2219/00051
See application file for complete search history.

(56) References Cited

U.S. PATENT DOCUMENTS

| | | | |
|---|---|---|---|
| 4,581,174 A | 4/1986 | Ohlinger et al. | |
| 5,931,579 A | 8/1999 | Gallus et al. | |
| 7,112,694 B2 | 9/2006 | Woelfert et al. | |
| 7,547,801 B2 * | 6/2009 | Pohl | C07C 263/10 560/347 |
| 8,079,752 B2 | 12/2011 | Rausch et al. | |
| 8,097,751 B2 | 1/2012 | Koch et al. | |
| 2007/0265465 A1 | 11/2007 | Keggenhoff et al. | |
| 2018/0364747 A1 * | 12/2018 | Charr | B01J 8/001 |

FOREIGN PATENT DOCUMENTS

EP 1873142 A1 1/2008
GB 1173890 * 12/1969

OTHER PUBLICATIONS

Cho et al, Kirk-Othmer Encyclopedia of Chemical Technology, Heat Transfer, 2000, John Wiley & Sons, Inc., pp. 242-281. (Year: 2000).*

* cited by examiner

*Primary Examiner* — Paul A Zucker
(74) *Attorney, Agent, or Firm* — Donald R. Palladino

(57) ABSTRACT

A process for preparing an isocyanate by reacting a primary amine with phosgene. The process includes providing an amine solution and adjusting its temperature in a heat exchanger, providing a phosgene solution and adjusting its temperature in a heat exchanger, mixing the amine solution with the phosgene solution, further conversion in an adiabatically operated reaction zone and the removing of the gas phase formed as a result of the chemical reaction in a separation zone, expanding the remaining liquid phase, further conversion of the liquid phase remaining after expansion in an indirectly heated reaction zone, and isolating the isocyanate from the obtained reaction solution. The temperature in the reaction zone and the temperature in the separation zone is adjusted by fixing a target value of 110° C. to 145° C. for the temperature of the reaction mixture and using the actual temperature of the reaction mixture for closed-loop control of the temperature of the solution of the primary amine and/or of the temperature of the solution of phosgene.

16 Claims, No Drawings

US 10,851,048 B2

PROCESS FOR PREPARING AN ISOCYANATE BY PARTLY ADIABATICALLY OPERATED PHOSGENATION OF THE CORRESPONDING AMINE

CROSS-REFERENCE TO RELATED APPLICATION

This application claims priority to European Application No. 18205954.3, filed Nov. 13, 2018, which is incorporated herein by reference.

FIELD

The present invention relates to a process for preparing an isocyanate by reacting a primary amine with phosgene, comprising I) providing an amine solution and adjusting its temperature in a heat exchanger, II) providing a phosgene solution and adjusting its temperature in a heat exchanger, III) mixing the amine solution with the phosgene solution in a mixing unit, followed by IV) further conversion in an adiabatically operated reaction zone and the removing of the gas phase formed as a result of the chemical reaction in a separation zone, V) expanding the remaining liquid phase, VI) further conversion of the liquid phase remaining after expansion in an indirectly heated reaction zone and VII) isolating the isocyanate from the reaction solution obtained therein, in which the temperature in the reaction zone and separation zone is adjusted by fixing a target value within a range from 110° C. to 145° C. for the temperature of the reaction mixture from step III) and using the actual temperature of the reaction mixture from step III) measured continuously or at intervals for closed-loop control of the temperature of the solution of the primary amine provided in step I) and/or of the temperature of the solution of phosgene provided in step II) by means of the heat exchangers used to adjust the temperature of each of these solutions.

BACKGROUND

Isocyanates (1) are prepared in large volumes and serve mainly as starting materials for production of polyurethanes. They are usually prepared by reacting the corresponding amines (2) with phosgene (3), using phosgene in a stoichiometric excess. The reaction of the amines with the phosgene can be effected either in the gas phase or in the liquid phase, wherein the reaction can be conducted batchwise or continuously. The phosgenation reaction—in the case of gas phase phosgenation after the quench of the gaseous reaction product obtained at first—gives a liquid phase comprising the desired isocyanate. As well as this liquid phase, gas streams are obtained at various points in the process, which, once they have been freed of products of value such as hydrogen chloride, phosgene, isocyanate and solvent as far as technically possible and economically viable, are generally sent to a phosgene breakdown in which trace fractions of phosgene that have not been removed in the preceding workup steps are broken down catalytically with water. In general, activated carbon is used as catalyst for the purpose. This phosgene breakdown gives a cleaned offgas and an acidic wastewater stream that has to be disposed of. This wastewater stream generally still contains organic impurities, for example solvent (typically monochlorobenzene in the case of preparation of MDI), amine (aniline in the case of preparation of MDI) and urea compounds. These organic impurities must be very substantially removed before wastewater can be sent to a wastewater treatment plant (for example a biological sewage plant). One way of achieving this is to bring the wastewater to a pH>7, especially in the range from 11 to 13, by addition of base (for example sodium hydroxide solution) and then to adsorb the organic impurities on activated carbon. Such an adsorption on activated carbon enables, in a simple manner, the reduction of the concentration of organic impurities in this wastewater stream to a level that allows the wastewater to be sent to a wastewater treatment plant.

Processes for preparing organic isocyanates from primary amines and phosgene have already been described many times before; merely by way of example, reference is made to the following documents:

DE-A-34 03 204 describes a continuous process for preparing organic polyisocyanates, in which elevated temperatures of 100 to 220° C. are established in a reaction involving partial circulation at a pressure of 5 to 100 bar.

DE-A-17 68 439 describes a process for continuously preparing organic isocyanates, in which the amine and phosgene feedstocks are first preheated and then the preheated constituents are combined in the reaction zone under high pressures and reacted under isothermal conditions, i.e. under heat exchange with the environment.

DE-A-102 22 968 describes a process for continuously preparing polyisocyanates by reacting primary amines with phosgene, in which the reaction is conducted in a cascade of temperature-adjustable reaction tubes of different size.

EP 1 873 142 A1 describes a three-stage process regime in which the pressure between the first stage of a mixer and the second stage of a first phosgenation reactor remains the same or rises and, in the third stage, an apparatus for phosgene removal, the pressure is lower than in the second stage. The reaction can be run adiabatically or isothermally.

Of interest on the industrial scale are both aromatic isocyanates, such as methylene diphenylene diisocyanate (MMDI henceforth—"monomeric MDI"), mixtures of MMDI and polymethylene polyphenylene polyisocyanates (i.e. the higher homologues of MMDI, PMDI henceforth, "polymeric MDI") or tolylene diisocyanate (TDI), and aliphatic isocyanates, for example pentane 1,5-diisocyanate (PDI), hexamethylene 1,6-diisocyanate (HDI) or isophorone diisocyanate (IPDI). In addition, isocyanates having benzylic isocyanate groups are also important; particular mention should be made here of xylylene diisocyanate (XDI). The present invention is especially concerned with the preparation of methylene diphenylene diisocyanates and polymethylene polyphenylene polyisocyanates (collectively called MDI henceforth).

In the majority of the known processes, the desired reaction temperature is established using temperature-controllable reactors in different variants (jacket heating, heating by heat exchangers or special reactor internals). In the isocyanate synthesis by phosgenation of amines, however, the external control of the temperature of the reactors often constitutes a problem since the high temperatures of the reactor wall surfaces promote or even actually cause the formation of by-products, which then adversely affect the yield and/or product properties. Moreover, deposits are then formed in the reactor, which necessitate regular shutdown and cleaning of the reactors. But this leads to a loss of plant capacity and hence to an economic disadvantage. Furthermore, the heat carrier systems incur additional capital costs, which likewise worsens the economic viability of the process. To solve these problems, EP 1 616 857 A1 proposes a two-stage process regime in which in a first stage a) amine and phosgene are reacted in an adiabatic reaction, where the reaction temperature is limited to values between 100 and 220° C. by setting the absolute pressure in the reactor specifically to values between 8 and 50 bar by expansion, and keeping the temperature at values between 100 and 220° C. until a conversion of phosgene of at least 80% has been attained, and then in a second stage b) expanding the reaction mixture from the first stage to absolute pressures in the range from 1 to 15 bar and continuing conversion at temperatures between 90 and 240° C., typically with supply of heat. Such a process regime can be referred to as an adiabatic-isothermal process regime. What is essential to the process described is the setting of the reaction temperature in the adiabatically operated reactor (100° C. to 220° C., preferably 115° C. to 180° C., more preferably 120° C. to 150° C.) via the pressure in this reactor. This setting via the pressure is effected via controlled expansion (see paragraph [0016]). There is no disclosure of setting of the temperature in the adiabatically operated reactor via targeted closed-loop control of reactant temperatures in EP 1 616 857 A1. The reaction mixture that leaves the adiabatically operated reactor is converted further in a second stage under isothermal conditions and expanded to a pressure below that in the first stage (cf. paragraph [0019]). At the outlet of the isothermally operated reactor, a gas phase and a liquid phase containing the isocyanate are withdrawn separately therefrom.

The quality of a process for preparing isocyanates is firstly defined by the content of unwanted by-products in the product of the process. Secondly, the quality of a process is defined in that the whole operation of startup and production in regular operation until the shutdown of the process can be executed without technical production outage and without problems that would necessitate intervention in the operation, and that there are no losses of feedstocks, intermediates or end product.

Ideally, therefore, the industrial scale plants for performance of such preparation processes are designed such that the processes run in a robust manner in the event of appropriate quality of the auxiliaries and feedstocks used and correct choice of process parameters such as pressure, temperature, ratios of amount and concentrations of the auxiliaries and feedstocks, etc. This means that, in such continuously operated large-scale plants, there will ideally be no problems such as the formation of precipitates, which can settle out in plant components and, for example, block pipelines. On the other hand, optimal exploitation of the space-time yield also contributes to a not inconsiderable degree to an improvement in productivity and hence the economic viability of industrial scale phosgenation plants. If the production rate enters the limiting ranges of what is still possible in a given plant, the process parameters must then be run within a very narrow window in order that there are none of the problems outlined above with precipitates, caking and product quality.

In summary, therefore, it can be stated that the open-loop and closed-loop control processes required for operation of a phosgenation plant should be optimized to bring about energy-efficient phosgenation with minimum apparatus complexity and with very substantial avoidance of the formation of deposits and by-products, especially in the reactor, and with simultaneous achievement of the desired product quality. Such an optimization of the phosgenation process also has a positive effect on the demand for solvent and the phosgene excess required. In this regard, there was still need for improvement over the prior art.

SUMMARY

Taking account of this need, the present invention provides a process for preparing an isocyanate by reacting a primary amine with phosgene, comprising the steps of:

I) providing a solution of the primary amine in a solvent and adjusting the temperature of the solution of the primary amine by indirect heat transfer in a heat exchanger operated with a heat carrier medium;

II) providing a solution of phosgene in a solvent and adjusting the temperature of the solution of phosgene by indirect heat transfer in a heat exchanger operated with a heat carrier medium;

III) mixing the solution of the primary amine provided in step I) and the solution of phosgene provided in step II) in a mixing unit to give a reaction mixture with observance of a stoichiometric excess of phosgene based on the amino groups of the primary amine in the range from 40% to 200% of theory, preferably in the range from 40% to 120% of theory, more preferably in the range from 50% to 100% of theory, most preferably in the range from 50% to 75% of theory;

IV) running the liquid reaction mixture obtained in step III) through a reaction zone and through a separation zone downstream in flow direction of this reaction zone to form a gas phase under a pressure in the range from 8.0 $bar_{(abs.)}$ to 50.0 $bar_{(abs.)}$, especially in the range from 15.0 $bar_{(abs.)}$ to 30.0 $bar_{(abs.)}$, from the liquid reaction mixture in the separation zone, where the reaction zone and the separation zone are not heated and not cooled, where the gas phase formed in the separation zone and the remaining liquid phase from the separation zone are removed separately from one another;

where the temperature in the reaction zone and separation zone is adjusted by fixing a target value within a range from 110° C. to 145° C. for the temperature of the reaction mixture from step III) and using the actual temperature of the reaction mixture from step III) measured continuously or at intervals for closed-loop control of the temperature of the solution of the primary amine provided in step I) to a value in the range from 30° C. to 130° C., especially in the range from 60° C. to 100° C., by means of the heat exchanger used in step I)

and/or (preferably and)

of the temperature of the solution of phosgene provided in step II) to a value in the range from −20° C. to 120° C., especially in the range from −10° C. to 30° C., by means of the heat exchanger used in step II);

V) expanding the liquid phase withdrawn from the separation zone from step IV) with partial conversion of this liquid phase to the gas phase;

VI) running the liquid phase that remains after the expansion in step V) through an indirectly heated reaction zone, forming a hydrogen chloride- and phosgene-containing gas phase (generally also still containing proportions of evaporated solvent) which is removed, and an isocyanate- and solvent-containing liquid phase remaining which is withdrawn from the indirectly heated reaction zone;

VII) working up the isocyanate- and solvent-containing liquid phase obtained in step VI) to recover the solvent and obtain the isocyanate.

DETAILED DESCRIPTION

According to the invention, the gas phase that forms in the separation zone is "under a pressure in the range from 8.0 $bar_{(abs.)}$ to 50.0 $bar_{(abs.)}$, especially in the range from 15.0 bar$_{(abs.)}$ to 30.0 bar$_{(abs.)}$". The chemical conversions that proceed in the reaction zone form an (at least) hydrogen chloride- and phosgene-containing gas phase from the liquid reaction mixture obtained in step III). The pressure values mentioned are thus based on the gas space of the separation zone. Here and hereinafter, all pressures should be understood as absolute pressures (identified as "bar$_{(abs.)}$").

Since the separation zone is "downstream in flow direction" of the reaction zone, which, in the terminology of the present invention, also means an open connection between the two zones for flow purposes, and since, moreover, the reaction zone and separation zone "are not heated and not cooled" (=adiabatic reaction regime), a temperature which, for a given temperature of the reaction mixture from step III), is determined essentially—apart from heat losses resulting from imperfect insulation of the apparatuses used—by the enthalpies of reaction of the chemical processes that proceed (which are elucidated in detail further down) is established at every point in the reaction zone and separation zone. The pressure that is established is also determined firstly by the chemical processes that proceed. Preferably, however, a pressure-retaining valve for the gas phase that forms and a closed-loop liquid level controller for the liquid phase are provided in the separation zone, in order to be able to reliably ensure that pressure is within the abovementioned range—8.0 bar$_{(abs.)}$ to 50.0 bar$_{(abs.)}$, especially in the range from 15.0 bar$_{(abs.)}$ to 30.0 bar$_{(abs.)}$—and, once set to a desired value within this range, remains constant during operation—with the possible exception of non-steady states such as changes in load or operational faults. Thus, however, the temperature in step IV) depends ultimately on the temperature of the reaction mixture to be fed to this step. According to the invention, the actual value of this temperature is measured continuously or at intervals and compared with a target value fixed beforehand within the range from 110° C. to 145° C. which is required in accordance with the invention. If the actual value measured differs significantly from the target value (which especially means a difference of more than 1.0° C., preferably of more than 0.5° C.), the temperature of the solution of the primary amine provided in step I) and/or the temperature of the solution of phosgene provided in step II) is adjusted appropriately (i.e. increased in the case of a downward deviation and lowered in the case of an upward deviation) in order to match the actual value to the target value. This is referred to within the scope of the terminology according to the invention as use of the measured actual temperature of the reaction mixture from step III) "for closed-loop control of the temperature of the solution of the primary amine provided in step I) . . . and/or of the temperature of the solution of phosgene provided in step II) . . . ". It is preferable here to correspondingly adjust both temperatures, i.e. the temperature of the solution of the primary amine provided in step I) and the temperature of the solution of phosgene provided in step II). This can be accomplished simultaneously (in parallel) or with a time delay.

The term "heat carrier medium" used in the terminology of the invention thus also includes the case that cooling is brought about by means of the heat exchanger (and reference could therefore also be made in this case to a "cooling medium").

On account of the adiabatic conditions in the reaction zone and separation zone from step IV), there is thus a reproducible correlation between the temperature of the reaction mixture from step III) supplied to the reaction zone from step IV) and the temperature in the reaction zone and separation zone, which can advantageously be determined as the temperature of the liquid phase leaving the separation zone.

According to the invention, phosgene, based on the amino groups of the primary amine, is used in a "stoichiometric excess". In theoretical terms, 1 mol of phosgene reacts with 1 mol of primary amino groups (1 R—NH$_2$+1 COCl$_2$→1 R—NCO+2 HCl). An excess of phosgene of x % over primary amino groups therefore corresponds to a molar ratio n(phosgene)/n(—NH$_2$) (n=molar amount) of $$\frac{1+\frac{x}{100}}{1},$$

i.e., for example, $$\frac{1+\frac{40}{100}}{1}=1.40$$

with a 40% excess of phosgene or for example $$\frac{1+\frac{120}{100}}{1}=2.2$$

with a 120% excess of phosgene.

There follows firstly a brief summary of various possible embodiments of the invention:

In a first embodiment of the invention, which can be combined with all other embodiments, the solution of the primary amine provided in step I) has a proportion by mass of primary amine based on the total mass of this solution in the range from 25% to 50%, especially in the range from 30% to 45%, and the solution of phosgene provided in step II) has a proportion by mass of phosgene based on the total mass of this solution in the range from 45% to 90%, especially in the range from 55% to 80%.

In a second embodiment of the invention, which can be combined with all other embodiments, the gas phases obtained in steps IV), V) and VI) are worked up to obtain hydrogen chloride and phosgene and optionally solvent.

In a third embodiment of the invention, which is a particular configuration of the second embodiment, the gas phases obtained in steps IV), V) and VI) are adjusted prior to the workup to a common pressure and combined.

In a fourth embodiment of the invention, which can be combined with all other embodiments, the mixing unit from step III) is not heated and not cooled.

In a fifth embodiment of the invention, which can be combined with all other embodiments, the mixing unit used in step III) comprises one or more dynamic mixers and especially does not comprise any static mixer.

In a sixth embodiment of the invention, which can be combined with all other embodiments, the reaction zone and separation zone from step IV) are disposed in a common reactor.

In a seventh embodiment of the invention, which is a particular configuration of the sixth embodiment, the reactor used is a tubular reactor in an upright arrangement (tube reactor, tower reactor).

In an eighth embodiment of the invention, which in a particular configuration of the seventh embodiment, the reaction mixture obtained in step III) flows through the reactor from the bottom upward.

In a ninth embodiment of the invention, which can be combined with all other embodiments, the indirectly heated reaction zone from step VI) is part of a shell and tube reactor (reactor having a multitude of reaction tubes arranged in a reactor vessel that encases them, so as to form a tube interior—the inside of the reaction tubes—and a tube exterior—the space between the reaction tubes, bounded on the outside by the inner wall of the encasing reactor vessel), the liquid phase remaining after the expansion in step V) is run through the tube interior thereof and a heating medium is run through the tube exterior thereof, or the liquid phase remaining after the expansion in step V) is run through the tube exterior thereof and a heating medium is run through the tube interior thereof.

In a tenth embodiment of the invention, which can be combined with all other embodiments, the heat exchangers used in step I) and in step II) are independently selected from the group consisting of shell and tube heat exchangers and plate heat exchangers, preference being given to using the same type of heat exchanger in both steps.

In an eleventh embodiment of the invention, which can be combined with all other embodiments, the heat exchangers used in step I) and in step II) are independently operated with a heat carrier medium selected from the group consisting of oil, salt melts, organic solvents and water, preference being given to organic solvents (preferably monochlorobenzene, dichlorobenzene or toluene, more preferably monochlorobenzene).

In a twelfth embodiment of the invention, which can be combined with all other embodiments, a pressure-retaining valve for the gas phase that forms and a closed-loop liquid level controller for the liquid phase are disposed in the separation zone from step IV), by means of which the pressure of the gas phase is kept constant.

In a thirteenth embodiment of the invention, which can be combined with all other embodiments, step IV) comprises the following:
  entering the target value for the temperature of the reaction mixture from step III) into an electronic data processing system;
  providing the measured values of the actual temperature of the reaction mixture from step III) in electronic form;
  transmitting the measured values provided in electronic form to the electronic data processing system;
  comparing the target value with the actual temperature in the electronic data processing system;
  if a deviation in the actual temperature from the target value by more than 1.0° C. (preferably by more than 0.5° C.) is found:
    in the event of an upward deviation reducing
    in the event of a downward deviation increasing
  the temperature of the heat carrier medium used in the heat exchangers by transmitting a corresponding command from the electronic data processing system to the temperature control device used to adjust the temperature of the heat carrier medium.

In a fourteenth embodiment of the invention, which can be combined with all other embodiments,
  (i) methylene diphenylene diisocyanate and/or polymethylene polyphenylene polyisocyanate is prepared by reacting methylene diphenylene diamine and/or polymethylene polyphenylene polyamine with phosgene or
  (ii) tolylene diisocyanate is prepared by reacting tolylenediamine with phosgene.

The embodiments briefly outlined above and further possible configurations of the invention are elucidated in detail hereinafter. Various embodiments are combinable with one another as desired unless the opposite is unequivocally apparent to the person skilled in the art from the context.

Step I) of the present invention, the providing of the amine solution required for the phosgenation, can be effected by any methods known from the prior art. The amine to be used is determined by the isocyanate desired. The process of the invention is suitable in principle for preparation of any desired aromatic, aliphatic and araliphatic isocyanates. Preference is given to using the process according to the invention for preparing methylene diphenylene diisocyanate (from methylene diphenylene diamine), polymethylene polyphenylene polyisocyanate (from polymethylene polyphenylene polyamine), mixtures of methylene diphenylene diisocyanate and polymethylene polyphenylene polyisocyanate (these mixtures are also referred to henceforth as MDI and the starting amine mixtures as MDA), tolylene diisocyanate (from tolylenediamine), xylylene diisocyanate (from xylylenediamine), pentane 1,5-diisocyanate (from pentane-1,5-diamine), hexamethylene diisocyanate (from hexamethylenediamine), isophorone diisocyanate (from isophoronediamine) and naphthyl diisocyanate (from naphthyldiamine), more preferably methylene diphenylene diisocyanate, mixtures of methylene diphenylene diisocyanate and polymethylene polyphenylene polyisocyanate, and tolylene diisocyanate. The process according to the invention is most preferably suitable for preparation of methylene diphenylene diisocyanate and mixtures of methylene diphenylene diisocyanate and polymethylene polyphenylene polyisocyanate. Methylene diphenylene diisocyanate is also referred to as diamine of the diphenylmethane series. Polymethylene polyphenylene polyisocyanate is also referred to as polyamine of the diphenylmethane series.

Processes for preparing the amines mentioned are known to those skilled in the art and therefore do not need any further elucidation at this point.

In step I), the amine to be phosgenated is dissolved in a solvent. This can be accomplished by means of mixing units known to the person skilled in the art, such as, more particularly, mixing tubes with static mixers as internals (frequently also referred to as static mixers for short). Suitable solvents usable in accordance with the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The solvent is preferably essentially free of isocyanate (target proportion by mass <100 ppm) and essentially free of phosgene (target proportion by mass <100 ppm), and this should be noted when using recycling streams Preference is therefore given to working by a process as described in EP 1 854 783 A2. The solvents can be used individually or in the form of any desired mixtures of the solvents mentioned by way of example. Preference is given to using monochlorobenzene (MCB) or ortho-dichlorobenzene (oDCB), most preferably monochlorobenzene (MCB).

An envisaged temperature of the resulting amine solution is in the range from 30° C. to 130° C., especially in the range from 60° C. to 100° C. This could in principle be achieved by appropriate control of the temperature of the amine and solvent starting materials, taking account of the enthalpy of dissolution. However, what is envisaged in accordance with the invention, especially in addition to said control of the temperature of the starting materials, is provision of a heat exchanger downstream of the mixing of amine and solvent, which enables the exact adjustment of the amine solution to the desired temperature in the range from 30° C. to 130° C., especially in the range from 60° C. to 100° C., which is thus able to heat or cool according to the temperature immediately downstream of the mixing of the starting materials. Heat exchangers known to those skilled in the art are suitable for this purpose, such as, in particular, shell and tube heat exchangers and plate heat exchangers, which correspondingly control the temperature of the solution by indirect heat transfer. For this purpose, the heat exchangers are operated with suitable heat carrier media, especially oil, salt melts, organic solvents (preferably monochlorobenzene, dichlorobenzene or toluene, particularly preferably monochlorobenzene or—less preferably, but also possible in principle—(heating or cooling) water. The heat carrier media used are adjusted to a temperature suitable for the respective requirement (heating or cooling). Temperature control devices suitable for this purpose, such as, in particular, shell and tube heat exchangers, plate heat exchangers and spiral heat exchangers, are known to those skilled in the art. The closed-loop control of the mode of operation of such a heat exchanger by the actual temperature of the reaction mixture from step (III) is a great advantage of the invention.

With regard to the amine concentration in the solution provided in step I), it is preferable to adjust the proportion by mass of primary amine based on the total mass of this solution to a value in the range from 25% to 50%, especially in the range from 30% to 45%.

Step II) of the present invention, the providing of the phosgene solution required for the phosgenation, can likewise be effected by any methods known from the prior art. Suitable mixing units and solvents are the same as described above for the primary amine. More particularly, it is preferable to dissolve the primary amine in step I) and phosgene in step II) in the same solvent in each case, i.e. most preferably in MCB. Processes for preparing phosgene are known to those skilled in the art and therefore do not need any further elucidation at this point.

An envisaged temperature of the resulting phosgene solution is in the range from −20° C. to 120° C., especially in the range from −10° C. to 30° C. This could in principle be achieved by appropriate control of the temperature of the phosgene and solvent starting materials, taking account of the enthalpy of dissolution. However, what is envisaged in accordance with the invention, especially in addition to said control of the temperature of the starting materials, is provision of a heat exchanger downstream of the mixing of phosgene and solvent, which enables the exact adjustment of the phosgene solution to the desired temperature in the range from −20° C. to 120° C., especially in the range from −10° C. to 30° C., which is thus able to heat or cool according to the temperature immediately downstream of the mixing of the starting materials. For this purpose, suitable heat exchangers are the same as described above for the primary amine; the remarks made there are therefore likewise applicable at this point. Preference is given to using the same type of heat exchanger, using the same type of heat carrier medium, in step I) and in step II). The closed-loop control of the mode of operation of such a heat exchanger by the actual temperature of the reaction mixture from step (III) is a great advantage of the invention.

With regard to the phosgene concentration in the solution provided in step II), it is preferable to adjust the proportion by mass of phosgene based on the total mass of this solution to a value in the range from 45% to 90%, especially in the range from 55% to 80%.

In step III) of the process according to the invention, the solution of the primary amine provided in step I) and the solution provided in step II) are mixed. Suitable mixing units for this purpose are those known to the person skilled in the art, such as static or dynamic mixers. Static mixers are characterized by the absence of moving parts; particular mention should be made here of mixing tubes with static mixers as internals (frequently also referred to as static mixers for short) or nozzles. By contrast, dynamic mixers contain moving parts, for example stirrer units. Particular mention should also be made here of the rotor-stator systems known from EP 0 830 894 A1 and EP 2 077 150 A1. Dynamic mixers, especially those of the rotor-stator type, are preferred for use in the present invention.

Preferably, the mixing unit from step III) is not heated and not cooled, meaning that the temperature of the reaction mixture obtained is determined solely by the enthalpy of mixing and the enthalpy of the reactions that have already set in in the mixing unit. A transport conduit for the reaction mixture between the exit from the mixing unit from step (III) and the entrance into the reaction zone from step (IV) is preferably likewise neither heated nor cooled, but is preferably thermally insulated.

According to the invention, in the mixing in step III), a stoichiometric excess of phosgene based on the amino groups of the primary amine in the range from 40% to 200% of theory, preferably in the range from 40% to 120% of theory, more preferably in the range from 50% to 100% of theory, most preferably in the range from 50% to 75% of theory, is observed.

In step IV) of the process according to the invention, the first main part of the reaction to give the isocyanate takes place, under adiabatic conditions. What this means is that the reaction mixture that passes through step IV) is neither heated nor cooled during the reaction. The apparatuses used are insulated against heat losses, such that the evolution of temperature is determined by the enthalpy of reaction of the reactions that proceed.

Without wishing to be tied to a theory, it can be assumed that several reactions run in parallel in step IV). The primary amine reacts with phosgene to give the known carbamoyl chloride intermediate (exothermic reaction). The hydrogen chloride released here reacts with as yet unconverted amine to give amine hydrochloride (exothermic reaction), which dissolves in the solvent used (endothermic reaction). The cleavage of the carbamoyl chloride to give the desired isocyanate and hydrogen chloride also already takes place in part in step IV) (endothermic reaction). The change in temperature depends on the interplay of all these reactions. In general, in step IV), only a small change in temperature is observed, which suggests that there is a "balance" of exo- and endothermic reactions. In any case, the reactions in step IV) form a gas phase, which is separated from the remaining liquid phase in the separation zone. Reaction zone and separation zone are preferably disposed in a common reactor. Suitable phosgenation reactors for this purpose are customary phosgenation reactors known to the person skilled in the art, such as in particular, tubular reactors in an upright arrangement (tube reactors; if the ratio of height to diameter is relatively small, reference is also made to tower reactors or reactor towers), through which the reaction mixture obtained in step III) preferably flows from the bottom upward. To narrow the dwell time distribution, the reactors in the reaction zone may be segmented by internals known to the person skilled in the art. In the upper part of the reactor, the gas phase formed and the remaining liquid phase are withdrawn separately. The phase separation takes place spontaneously.

According to the invention, a target value in the range from 110° C. to 145° C. is fixed for the temperature of the reaction mixture from step III). A suitable target value (in the sense of minimized by-product formation and minimized solvent input) is dependent on the isocyanate to be prepared and plant parameters and can be ascertained easily by the person skilled in the art for a given production plant by preliminary experiments. The temperature that actually exists (actual temperature) can be measured with temperature sensors known to those skilled in the art, which are mounted at an appropriate point (especially at the exit of the mixing unit from step III).

The inventive adjustment of the temperature in the reaction zone and separation zone is then effected by measuring the temperature of the reaction mixture leaving the mixing unit from step III) and comparing it with a previously fixed target value within the range from 110° C. to 145° C. and levelling out differences found by increasing or lowering the temperature of the solution of the primary amine provided in step I) and/or the temperature of the solution of phosgene provided in step II).

For this purpose, the heat exchangers in each case connected downstream of the mixing of amine and solvent and downstream of the mixing of phosgene and solvent that have been mentioned further up are used. According to the invention, deviations found from the target value of the temperature of the reaction mixture leaving the mixing unit from step III) are thus levelled out by increasing or lowering the temperature of the solution of the primary amine provided in step I) and/or of the solution of phosgene provided in step II), by feeding the solution of the primary amine provided in step I) and the solution of phosgene provided in step II) to the mixing unit from step III) via a heat exchanger in each case, and by bringing about the increase or lowering of the temperature of the solution of the primary amine provided in step I) and/or of the solution of phosgene provided in step II) by an appropriate change in the mode of operation of the respective heat exchanger (enhanced heating, enhanced cooling or even reversal of the heating mode to cooling mode or of the cooling mode to heating mode).

Particular preference is given here to the following automated procedure for step IV):
  entering the target value for the temperature of the reaction mixture from step III) into an electronic data processing system;
  providing the measured values of the actual temperature of the reaction mixture from step III) in electronic form;
  transmitting the measured values provided in electronic form to the electronic data processing system;
  comparing the target value with the actual temperature in the electronic data processing system;
  if a deviation in the actual temperature from the target value by more than 1.0° C. (preferably by more than 0.5° C.) is found:
    in the event of an upward deviation reducing
    in the event of a downward deviation increasing
    the temperature of the heat carrier medium used in the heat exchangers by transmitting a corresponding command from the electronic data processing system to the temperature control device used to adjust the temperature of the heat carrier medium.

Suitable hardware and software for the implementation of this embodiment is known to the person skilled in the art.

In step V) of the process according to the invention, the liquid process product obtained in step IV) is expanded to a lower pressure, preferably to a pressure in the range from 1.0 $bar_{(abs.)}$ to 20 $bar_{(abs.)}$, preferably 1.0 $bar_{(abs.)}$ to 5.0 $bar_{(abs.)}$, measured in the gas phase. Suitable apparatuses for this purpose are apparatuses known to the person skilled in the art, such as, in particular, gas-liquid separation vessels (also referred to as gas separators). This forms a gas phase containing hydrogen chloride and unconverted phosgene. The apparatus used can also be disposed within the same apparatus as the indirectly heated reaction zone from step VI); in this regard, see also the elucidations that follow relating to step VI).

In step VI), the liquid phase remaining after the expansion in step IV) is converted further in an indirectly heated reaction zone to form a hydrogen chloride- and phosgene-containing gas phase ("isothermal process regime"). This can take place in heatable reactors known to the person skilled in the art. Especially suitable for this purpose are shell and tube reactors (in a vertical arrangement). The liquid phase from step IV) can be run here through the interior of the tubes of the shell and tube reactor (tube interior) or through the space between the tubes of the shell and tube reactor which is bounded on the outside by the reactor wall that encases the bundle of tubes (tube exterior). The heating medium—a heat carrier oil, a salt melt, steam or the like—is then run through the respective other space, such that it does not come into physical contact with the liquid process product to be converted (indirect heating). The liquid phase from the expansion from step IV) here runs through the shell and tube reactor in a vertical arrangement preferably from the top downward. In the preferred configuration of the invention with integration of the apparatus envisaged for the expansion stage of step IV) into the apparatus from step V) containing the indirectly heated reaction zone, the expansion then takes place with gas-liquid phase separation in a dome at the top of the shell and tube reactor.

In steps IV), V) and VI), gas phases containing hydrogen chloride and phosgene, with or without solvent, are obtained. These gas phases are preferably worked up to recover products of value. For this purpose, it is appropriate to adjust the gas phases obtained prior to the workup to a common pressure and combine them. This workup can be accomplished as known in the prior art.

The process according to the invention results at least in the following advantages without impairing product quality with regard to secondary component formation, colour, acidity, NCO content and iron content:

i) improvement in the energy efficiency of the process by optimization of the formulation with regard to the ratio of solvent to amine (reduction in the amount of solvent to be recycled);

ii) The closed-loop control via the temperature of the reaction mixture from step III) is easy to implement and enables better quality control (the colour of the product and the secondary component content can easily be kept to acceptable values; it is thus also possible in what is called the polymer removal—the distillative removal of a fraction containing methylene diphenylene diisocyanate from a mixture containing polymethylene polyphenylene polyisocyanate and methylene diphenylene diisocyanate—to remove more methylene diphenylene diisocyanate by distillation without changing the composition of the desired polymer type [since the yield of monomeric MDI is increased owing to reduced by-product formation]).

The success of the procedure according to the invention for controlling the phosgenation reaction in an "adiabatic-isothermal mode of operation" by means of closed-loop temperature control of the feed streams of amine solution and/or phosgene solution was surprising to the person skilled in the art since there have been no reports to date regarding complications with increasing temperature in the phosgenation as a result of exothermic reactions (which of course already occur in the mixing unit from step III)). The closed-loop temperature control system described enables phosgenation reactions with a particularly low solvent level. Less energy is then consumed for recycling of excess solvent, and product quality rises.

The invention is elucidated in detail hereinafter by examples.

Examples 1 to 4

The temperatures of the amine solution and phosgene solution were varied in order to examine the effect on the quality of the product obtained (colour values, NCO index and acidity). The operating conditions can be found in Table 1.

As can be seen, the colour values, NCO index and acidity value are best overall when the exit temperatures of amine solution and phosgene solution (which determine the mixer exit temperature under given boundary conditions) are low (Example 4). This shows the great significance of the process according to the invention, which enables rapid counteraction in the event of unwanted deviations in the mixer exit temperature in a simple manner and adjustment in this way of the temperature in the reactor of step IV).

TABLE 1

Operating conditions and results in Examples 1 to 4

| Example | T(MDA soln.)/ °C. | T(COCl$_2$) soln./ °C. | T(mixer exit)/ °C. | Yellow value E430 | Grey value E520 | NCO value/ % | Acidity/ ppm |
|---|---|---|---|---|---|---|---|
| 1 | 120 | −2.0 | 141.0 | 0.131 | 0.032 | 30.6 | 403 |
| 2 | 100 | 63 | 139.0 | 0.306 | 0.115 | 30.6 | 200 |
| 3 | 60 | 80 | 139.0 | 0.281 | 0.102 | 30.9 | 120 |
| 4 | 60 | −2.0 | 129.0 | 0.108 | 0.036 | 31.2 | 39 |

EXAMPLES

General Procedure for the Performance of Examples 1 to 4

MDA and MCB are mixed continuously to give a 30% MDA solution. Phosgene and MCB are likewise mixed continuously to give a 60% phosgene solution. The temperatures of the MDA and phosgene solutions obtained are each adjusted by means of a heat exchanger. The MDA solution (64 kg/h) and phosgene solution (51 kg/h) are continuously mixed dynamically (barbed mixer), with a phosgene excess of 60% of theory in each case. The pressure in the barbed mixer is 22.0 bar$_{(abs.)}$. The exit temperature of the reaction mixture beyond the barbed mixture is established as a result of the interplay of exo- and endothermic reactions, i.e. depends on the progress of the reaction that exists under the respective conditions. The reaction mixture leaving the barbed mixer is run under essentially the same pressure (i.e. 22.0 bar$_{(abs.)}$ plus a comparatively small fraction of the hydrostatic pressure) through a first tube reactor R1 in an upright arrangement that is neither heated nor cooled but is insulated against heat losses. After a dwell time of 2.0 min, a gas phase and a liquid phase are withdrawn at different points from the reactor R1 in the upper region (separation zone). The temperature of the liquid phase withdrawn at the exit from R1 under the reaction conditions chosen is not very different from the entrance temperature (deviation ±5.0° C.), which indicates that exo- and endothermic reactions in reactor R1 are roughly in balance. The liquid phase is expanded in a gas separator to a pressure of 2.0 bar$_{(abs.)}$, and the liquid phase that leaves the gas separator is run through a second, indirectly heated tubular reactor R2. The dwell time in the second reactor R2 is chosen such that the cleavage of carbamoyl chloride is virtually complete. The liquid phase leaving the second reactor is freed of phosgene, hydrogen chloride and MCB according to the prior art.

Methods of Analysis:

Colour (yellow value, grey value): Preparation of an about 2% solution (based on mass) of the sample in monochlorobenzene, determination of absorbance at 430 nm (E430, yellow value) and at 520 nm (E520, grey value) with the aid of a UV/VIS spectrophotometer using a cuvette having a path length of 1 cm.

NCO value: Reaction with dibutylamine and back-titration of the unconverted dibutylamine with a standard HCl solution.

Acidity: Dissolving about 6 g of sample in 40 ml of monochlorobenzene, adding 100 ml of methanol and stirring at room temperature for 30 min. Titration with standard methanolic KOH solution.

Example 5 (Inventive): Computer Simulation of the Process According to the Invention for Production on the Industrial Scale In an MDI plant, 40.0 t/h of MDA at a temperature of 130° C. are mixed with 94.5 t/h of MCB at a temperature of 52° C. as solvent by means of a static mixer to give a 30.0% MDA solution (step I)). Phosgene is mixed with MCB in a phosgene dissolution tank to obtain a 60.0% phosgene solution (step II)). 106.7 tonnes per hour of this phosgene solution at a temperature of 3.0° C. are run through a heat exchanger and thus cooled down to a temperature of −1° C. In an analogous manner, 134.5 tonnes per hour of the 30% MDA solution at a temperature of 80.0° C. are run through a heat exchanger and thus cooled down to a temperature of 60° C. The MDA and phosgene solutions having temperatures thus adjusted are run into a dynamic mixer (step III)). The temperature at the exit of the dynamic mixer is adjusted to 130° C.

The liquid reaction mixture leaving the mixer is run under adiabatic conditions through a phosgenation reactor (tower reactor) insulated against heat losses (step IV)). The pressure at the exit from the phosgenation reactor is adjusted by means of a pressure-retaining valve to 22 bar$_{(abs.)}$; the exit temperature is 120° C. The dwell time of the phosgenation reaction from the mixer to the exit from the phosgenation reactor is 5 min. At the top of the tower reactor, an HCl- and phosgene-containing gas phase (also still containing fractions of evaporated MCB) separates out. The reaction solution withdrawn from the reactor is expanded in a gas separator to 3 bar$_{(abs.)}$ (step V)) and then converted further in a heated reactor at 130° C. and 3 bar$_{(abs.)}$ (step VI)).

Subsequently, the reaction solution leaving the heated reactor is worked up with recycling of the solvent to obtain the isocyanate (step VII)). The workup comprises a dephosgenation and removal of solvent. In the distillation for removal of solvent, the bottom product obtained is 50.0 t/h of MDI, which is separated by means of further distillation steps into methylene diphenylene diisocyanate and a mixture of methylene diphenylene diisocyanate and polymethylene polyphenylene polyisocyanate.

The temperature in the tower reactor is adjusted by measuring the mixer exit temperature and controlling the temperature of the MDA solution or phosgene solution in such a way that, in the event of a significant deviation from the target temperature of 130° C., the mode of operation of the corresponding heat exchangers is altered such that the target value of 130° C. is attained again as rapidly as possible. The two heat exchangers are thus controlled via the temperature at the mixer exit, which means that they are heated or cooled as required, as a result of which the temperatures of the phosgene solution and MDA solution required to attain the desired mixer exit temperature of 130° C. are established. This procedure keeps the temperature at the exit from the phosgenation reactor constant at 120° C.

In a real production plant, the flow rates mentioned here can advantageously be implemented in multiple reaction lines operated in parallel.

The invention claimed is:

1. A process for preparing an isocyanate by reacting a primary amine with phosgene, comprising:
   I) providing a solution of the primary amine in a solvent and adjusting the temperature of the solution of the primary amine by indirect heat transfer in a heat exchanger operated with a heat carrier medium;
   II) providing a solution of phosgene in a solvent and adjusting the temperature of the solution of phosgene by indirect heat transfer in a heat exchanger operated with a heat carrier medium;
   III) mixing the solution of the primary amine and the solution of phosgene in a mixing unit to give a reaction mixture having a stoichiometric excess of phosgene based on the amino groups of the primary amine in the range from 40% to 200% of theory;
   IV) running the reaction mixture through a reaction zone and through a separation zone that is arranged downstream in the flow direction of the reaction zone to form a gas phase under a pressure of 8.0 bar$_{(abs.)}$ to 50.0 bar$_{(abs.)}$, wherein the reaction zone and the separation zone are not heated and are not cooled, and wherein the gas phase and remaining liquid phase from the separation zone are removed separately from one another;
   V) expanding the liquid phase withdrawn from the separation zone with partial conversion of the liquid phase to the gas phase;
   VI) running the liquid phase that remains after the expansion through an indirectly heated reaction zone, thereby forming:
      (a) a hydrogen chloride and phosgene-containing gas phase which is removed, and
      (b) an isocyanate- and solvent-containing liquid phase which is withdrawn from the indirectly heated reaction zone; and
   VII) working up the isocyanate- and solvent-containing liquid phase to recover the solvent and obtain the isocyanate;
   where the process comprises adjusting the temperature in the reaction zone and the temperature in the separation zone by fixing a target temperature of 110° C. to 145° C. for the temperature of the reaction mixture and using the actual temperature of the reaction mixture, measured continuously or at intervals, for closed-loop control of at least one of:
      (a) the temperature of the solution of the primary amine to a temperature of 30° C. to 130° C. by means of the heat exchanger used in step I); and
      (b) the temperature of the solution of phosgene to a temperature of −20° C. to 120° C. by means of the heat exchanger used in step II).

2. The process of claim 1, in which the solution of the primary amine provided in step I) has a proportion by mass of primary amine based on the total mass of thereof of 25% to 50% and the solution of phosgene provided in step II) has a proportion by mass of phosgene based on the total mass of thereof of 45% to 90%.

3. The process of claim 1, in which the gas phases obtained in steps IV), V) and VI) are worked up to obtain hydrogen chloride and phosgene and optionally solvent.

4. The process of claim 3, in which the gas phases obtained in steps IV), V) and VI) are, prior to the workup, adjusted to a common pressure and combined.

5. The process of claim 1, in which the mixing unit from step III) is not heated and not cooled.

6. The process of claim 1, in which the mixing unit used in step III) comprises one or more dynamic mixers.

7. The process of claim 1, in which reaction zone and separation zone from step IV) are disposed in a common reactor.

8. The process of claim 7, in which the reactor is a tubular reactor in an upright arrangement.

9. The process of claim 8, in which the reaction mixture obtained in step III) flows through the reactor from the bottom upward.

10. The process of claim 1, in which the indirectly heated reaction zone from step VI) is part of a shell and tube reactor, the liquid phase remaining after the expansion in step V) is run through the tube interior thereof and a heating medium is run through the tube exterior thereof, or the liquid phase remaining after the expansion in step V) is run through the tube exterior thereof and a heating medium is run through the tube interior thereof.

11. The process of claim 1, in which the heat exchangers used in step I) and in step II) are independently selected from the group consisting of shell and tube heat exchangers and plate heat exchangers.

12. The process of claim 1, in which the heat exchangers used in step I) and in step II) are independently operated with a heat carrier medium selected from the group consisting of oil, salt melts, organic solvents and water.

13. The process of claim 1, in which a pressure-retaining valve for the gas phase that forms and a closed-loop liquid level controller for the liquid phase are disposed in the separation zone from step IV), by means of which the pressure of the gas phase is kept constant.

14. The process of claim 1, in which:
(i) methylene diphenylene diisocyanate and/or polymethylene polyphenylene polyisocyanate is prepared by reacting methylene diphenylene diamine and/or polymethylene polyphenylene polyamine with phosgene, or
(ii) tolylene diisocyanate is prepared by reacting tolylenediamine with phosgene.

15. The process of claim 1, in which adjusting the temperature in the reaction zone and the temperature in the separation zone comprises closed-loop control of
  (a) the temperature of the solution of the primary amine; and
  (b) the temperature of the solution of phosgene.

16. The process of claim 15, in which adjusting the temperature in the reaction zone and the temperature in the separation zone comprises:
  entering the target value for the temperature of the reaction mixture from step III) into an electronic data processing system;
  providing the measured values of the actual temperature of the reaction mixture from step III) in electronic form;
  transmitting the measured values provided in electronic form to the electronic data processing system;
  comparing the target value with the actual temperature in the electronic data processing system;
  if a deviation in the actual temperature from the target value by more than 1.0° C. is found, then:
    in the event of an upward deviation reducing, or
    in the event of a downward deviation increasing
    the temperature of the heat carrier medium used in the heat exchangers by transmitting a corresponding command from the electronic data processing system to the temperature control device used to adjust the temperature of
    (a) the heat carrier medium used to operate the heat exchanger used in step I); and
    (b) the heat carrier medium used to operate the heat exchanger used in step II).

* * * * *